US00PP33429P2

(12) United States Plant Patent
Bruinen

(10) Patent No.: US PP33,429 P2
(45) Date of Patent: Aug. 31, 2021

(54) ***ZAMIOCULCAS* PLANT NAMED 'EDZAM1702'**

(50) Latin Name: ***Zamioculcas zamiifolia* (hort. Lodd.) Engl.**
Varietal Denomination: EDZAM1702

(71) Applicant: ED HOLDING B.V., Maasdijk (NL)

(72) Inventor: Ed Bruinen, Maasdijk (NL)

(73) Assignee: Ed Holding B. V., Maasdijk (NL)

( * ) Notice: Subject to any disclaimer, the term of this patent is extended or adjusted under 35 U.S.C. 154(b) by 0 days.

(21) Appl. No.: 16/873,565

(22) Filed: May 6, 2020

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373, 263.1
CPC ..... A01H 5/12; A01H 5/00
See application file for complete search history.

(56) References Cited

PUBLICATIONS

PLUTO UPOVROM Plant Variety Database Citation for 'EDZAM1702' as per QZ PBR 20173140; Dec. 1, 2017; 1 page.*

* cited by examiner

*Primary Examiner* — Kent L Bell
(74) *Attorney, Agent, or Firm* — Samuel R. McCoy, Jr.

(57) ABSTRACT

'EDZAM1702' is a new and distinctive *Zamioculcas* plant which is characterized by a very large plant size, with an abundance of leaves comprised of dark green and glossy leaflets born on long light green petioles. The new plant propagates successfully by leaf cuttings and has shown to be uniform and stable in the resulting generations from asexual propagation.

2 Drawing Sheets

Latin name of the genus and species: The Latin name of the genus and species of the novel variety disclosed herein is *Zamioculcas zamiifolia* (hort. Lodd.) Engl.

Variety denomination: The inventive variety of *Zamioculcas* disclosed herein has been given the variety denomination 'EDZAM1702'.

BACKGROUND OF THE INVENTION

Parentage: 'EDZAM1702' is a seedling selection resulting from the controlled pollination of a first unnamed and unpatented *Zamioculcas zamiifolia* plant, the seed parent, with a second unnamed and unpatented *Zamioculcas zamiifolia* plant, the pollen parent, at a commercial nursery in Maasdijk, The Netherlands, in the summer of 2014. In the summer of 2015, one plant was observed to exhibit unique growth characteristics and was isolated for further evaluation in order to confirm the distinctness and stability of the characteristics first observed. Upon confirmation of distinctness and stability, 'EDZAM1702' was selected for commercialization.

Asexual Reproduction: Asexual reproduction of 'EDZAM1702' was first accomplished in 2015 by way of stem cuttings at a commercial greenhouse in Maasdijk, The Netherlands. Four successive generations produced from stem cuttings have shown that the unique features of the instant cultivar are stable and reproduce true to type.

SUMMARY OF THE INVENTION

The cultivar 'EDZAM1702' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Zamioculcas* plant, 'EDZAM1702'. These traits, in combination, distinguish 'EDZAM1702' as a new and distinct cultivar.

1. *Zamioculcas* 'EDZAM1702' exhibits a large plant size; and
2. *Zamioculcas* 'EDZAM1702' exhibits an abundance of foliage; and
3. *Zamioculcas* 'EDZAM1702' exhibits dark green and glossy leaflets borne on long, light green petioles.

BOTANICAL DESCRIPTION OF THE PLANT

Figure 1:
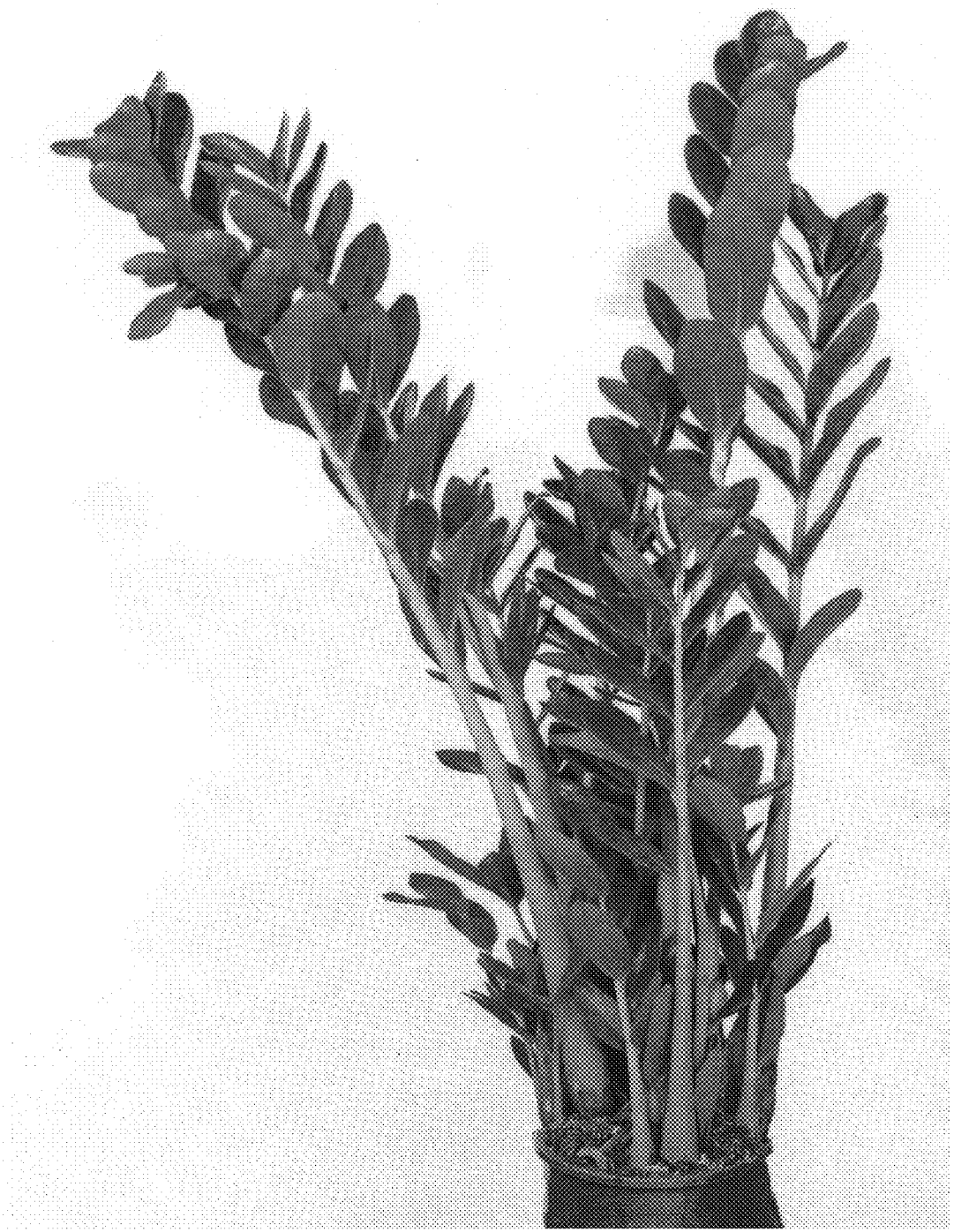
FIG. 1 shows, as nearly true as it is reasonably possible to make the same in color illustrations of this type, the typical foliage and growth characteristics of the new cultivar, 'EDZAM1702'. The plant shown is approximately 30 months old, potted into a 17 cm nursery pot, grown at a commercial greenhouse in Maasdijk, The Netherlands.
Figure 2:
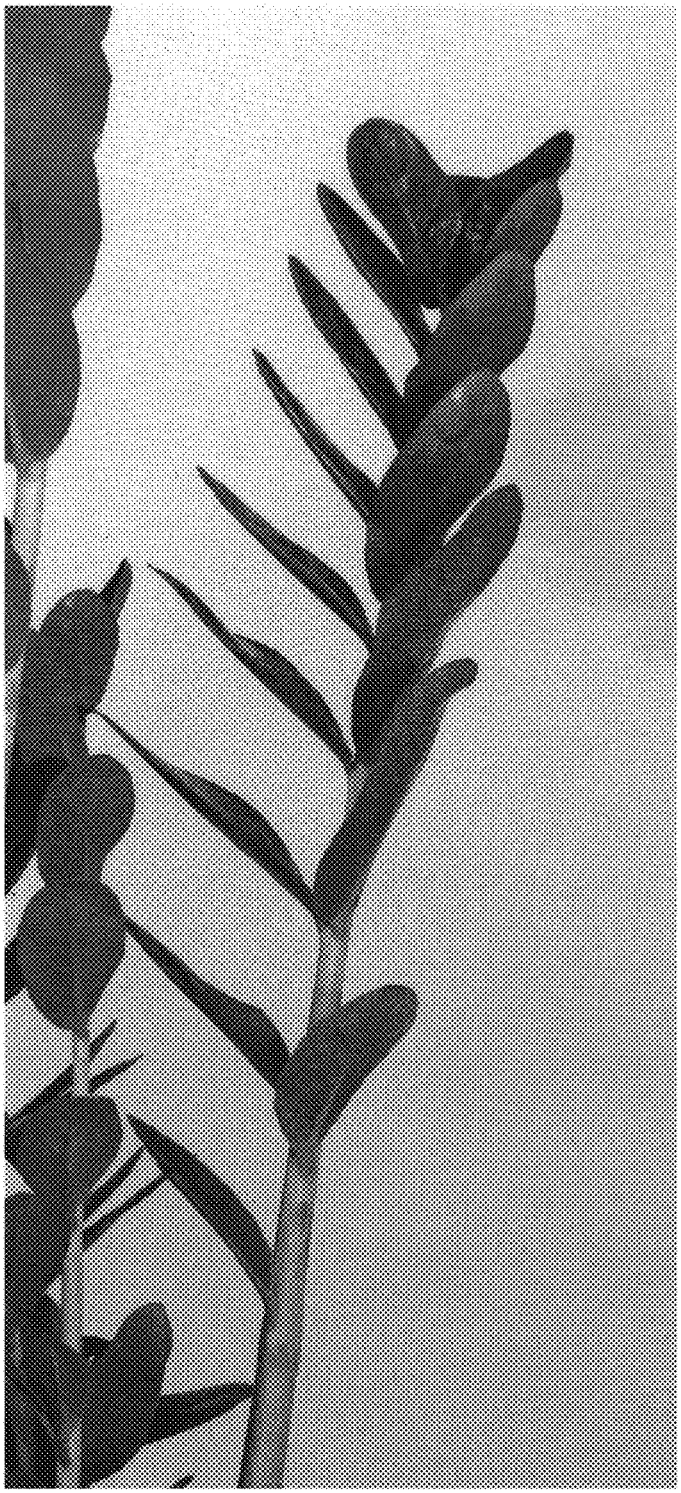
FIG. 2 shows, as nearly true as it is reasonably possible to make the same in color illustrations of this type, the typical foliage of the plant in FIG. 1.

The following is a detailed botanical description of a new and distinct variety of *Zamioculcas zamiifolia* known as 'EDZAM1702', based upon observations of 30 month-old plants, potted into 17 cm nursery pots and grown indoors at a commercial nursery in Maasdijk, The Netherlands. Plants were grown in full sun using accepted fertility and irrigation practices for *Zamioculcas* plants. With the exception of preventative fungicides, no chemical pest control measures were employed. Furthermore, no artificial light or photoperiodic treatments were given to the plants. Observation data was recorded in October of 2019.

Those skilled in the art will appreciate that certain characteristics will vary with older or, conversely, with younger plants. 'EDZAM1702' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'EDZAM1702' and comparisons with the parent plants and the most similar variety of common knowledge are provided below.

General plant description:

*Growth habit*.—Tropical evergreen perennial.

*Plant profile shape*.—Narrow inverted triangular to obovate.

*Growth rate*.—Moderately fast to fast growing.

*Plant vigor*.—Moderately vigorous to highly vigorous.

*Height*.—74.3 cm to the top of the foliar plane.

*Width*.—61.8 cm.

*Propagation*.—Type — Leaf cuttings. Time to initiate rooting — Approximately 30 days at an approximate temperature of 25 degrees Celsius. Crop time — Approximately 1 year to produce a marketable plant in an 11 cm container.

*Pathogen and pest resistance and susceptibility*.—Plants have not been observed to be susceptible or resistant to pathogens and pests common to *Zamioculcas* sp.

*Environmental tolerances*.—Adapt to, at least, USDA Zones 10 to 12 and temperatures ranging from 5 to 40 degrees Celsius; moderate tolerance to rain; low tolerance to wind.

Stem:

*Branching habit*.—No stems or branches; compound leaves in small clumps, arising directly from tuberous rhizomes.

*Number of clumps per plant*.—Five, on average.

*Number of additional clumps formed each year*.—Five, on average.

Root system:

*Type*.—Tuberous rhizomes bearing thick fleshy roots.

*Shape of rhizomes*.—Irregular oblong to ovoid.

*Dimensions of rhizomes*.—8.2 cm long and 6.5 cm in diameter.

*Density of rhizomes and roots*.—Moderately dense.

*Distribution of rhizomes and roots*.—Rhizomes shallow; roots distributed evenly throughout the soil profile, from shallow to deep.

*Texture of rhizomes and roots*.—Glabrous and very fleshy.

*Color of rhizomes and roots*.—Greyed-green, nearest to a mixture of RHS 195A, 195B, and 195C.

Foliage:

*Arrangement*.—Compound leaves in small clumps, arising directly from tuberous rhizomes.

*Attachment*.—Petiolate.

*Division*.—Pinnately compound.

*Leaf profile shape*.—Narrow oblong.

*Dimensions*.—64.8 cm long and 14.7 cm wide.

*Attitude*.—Upright; approximately 10 degrees from vertical.

*Quantity*.—Approximately 5 leaves per clump.

*Stipules*.—General — A leafy stipule is present at the base of each pinnately compound leaf. Shape — Narrow ovate. Length — 14.9 cm. Width — 4.7 cm. Apex — Acute. Base — Broad cuneate. Margin — Entire, moderately undulated. Texture — Papery. Color, adaxial and abaxial surfaces — Translucent greyed-brown; nearest to a mixture of RHS 199A, 199B, 199C and 199D.

*Petiole*.—Aspect — Ovate. Length — 26.4 cm; 59.8 cm, including all rachises. Diameter — 3.2 cm at the base; 2.0 cm below the first leaflet. Strength — Strong. Texture — Smooth and glabrous. Luster — Matte. Color, adaxial and abaxial surfaces — Yellow-green, nearest to RHS 147D and slightly darker distally, nearest to in between RHS 147B and 147C.

*Rachis*.—Aspect — Ovate. Length — 33.4 cm. Diameter — 1.25 cm at the widest point; 1.1 cm at the narrowest point. Strength — Strong. Texture — Smooth and glabrous. Luster — Matte. Color, adaxial surface — Yellow-green, nearest to RHS 147D; sparsely and irregularly blotched with a darker shade of yellow-green, nearest to in between RHS 147B and 147C yet closest to 147C. Color, abaxial surface — Yellow-green, nearest to RHS 147D; moderately and irregularly blotched in between greyed-green and brown, RHS 197A and N200B, and lightly suffused with yellow-green, RHS 147A.

*Leaflets*.—Quantity — Typically 16 leaflets. Attitude — At an angle of approximately 60 degrees to the rachis. Dimensions — 9.8 cm long and 4.7 cm wide. Shape — Obovate to elliptic. Aspect — Slightly carinate and lightly curled inward. Apex — Abruptly acute. Base — Obtuse. Margin — Entire; very slightly undulated. Texture, adaxial surface — Glabrous and moderately coriaceous. Texture, abaxial surface — Glabrous and moderately coriaceous. Luster, adaxial surface — Very glossy. Luster, abaxial surface — Glossy. Color — Juvenile foliage color, adaxial surface — Green, nearest to RHS NN137A. Juvenile foliage color, abaxial surface — Nearest to in between green and yellow-green, yet darker and more intense; RHS 143A and 146A. Mature foliage color, adaxial surface — Nearest to yellow-green, RHS NN137A, yet darker. Mature foliage color, abaxial surface — Yellow-green, nearest to RHS 146A, yet slightly darker. Venation — Pattern — Pinnate. Vein color, adaxial surface — Green, nearest to RHS 143C. Vein color, abaxial surface — Yellow-green, nearest to in between RHS 144B and 144C. Petiolule — Aspect — Flattened oval. Length — 0.8 cm. Diameter — Petioles flattened; average width is 0.45 cm and the average height is 0.35 cm. Strength — Strong. Color, adaxial surface — Yellow-green, nearest to in between RHS 146A and 146B. Color, abaxial surface — Yellow-green, nearest to RHS 1466. Texture, adaxial and abaxial surfaces — Smooth and glabrous. Luster, adaxial and abaxial surfaces — Matte.

Inflorescence: No flowering has been observed to date.

COMPARISON WITH THE PARENT PLANTS

Plants of the new cultivar 'EDZAM1702' may be distinguished from its seed parent, an unnamed *Zamioculcas zamiifolia* plant, by the characteristics described in Table 1.

TABLE 1

Comparison Between 'EDZAM1702' and The Seed Parent

| Characteristic | 'EDZAM1702' | The Seed Parent |
|---|---|---|
| Amount of leaf-bearing clumps. | Fewer clumps per plant than the parent. | More clumps per plant than 'EDZAM1702'. |
| Leaflet shape. | Less elliptic; closer to obovate. | More elliptic. |
| General coloration of the foliage. | Lighter shade of green compared to the parent. | Darker shade of green compared to 'EDZAM1702'. |

Plants of the new cultivar 'EDZAM1702' may be distinguished from its pollen parent, an unnamed *Zamioculcas zamiifolia* plant, by the characteristics described in Table 2.

TABLE 2

Comparison Between 'EDZAM1702' and The Pollen Parent

| Characteristic | 'EDZAM1702' | The Pollen Parent |
|---|---|---|
| Amount of leaf-bearing clumps. | More clumps per plant than the parent. | Fewer clumps per plant than the parent. |
| Leaflet shape. | More elliptic. | Less elliptic; closer to obovate. |

TABLE 2-continued

Comparison Between 'EDZAM1702' and The Pollen Parent

| Characteristic | 'EDZAM1702' | The Pollen Parent |
|---|---|---|
| General coloration of the foliage. | Darker shade of green compared to the parent. | Lighter shade of green compared to 'EDZAM1702'. |

COMPARISONS WITH THE MOST SIMILAR VARIETY OF COMMON KNOWLEDGE

Plants of the new cultivar 'EDZAM1702' are most similar to the commercial variety, *Zamioculcas* 'EDZAMVIG1' (Community Plant Variety Rights grant number 45882). A comparison of 'EDZAM1702' with 'EDZAMVIG1' is described in Table 3.

TABLE 3

Comparison Between 'EDZAM1702' and 'EDZAMVIG1'

| Characteristic | 'EDZAM1702' | 'EDZAMVIG1' |
|---|---|---|
| Leaf attitude. | More relaxed than 'EDZAMVIG1'. | More upright than 'EDZAM1702'. |
| Leaflet shape. | More elliptic. | Less elliptic; closer to obovate. |
| Leaflet aspect. | Slightly carinate and lightly curled inward. | Slightly carinate and more strongly curled inward. |
| Leaflet margins. | Lightly undulated. | Moderately undulated. |
| General coloration of the foliage. | Darker shade of green compared to 'EDZAMVIG1'. | Lighter shade of green compared to 'EDZAM1702'. |

That which is claimed is:

1. A new and distinct variety of *Zamioculcas* plant named 'EDZAM1702', substantially as described and illustrated herein.

* * * * *